United States Patent
Romo et al.

(10) Patent No.: US 9,597,786 B2
(45) Date of Patent: Mar. 21, 2017

(54) TORQUE LIMITING TOOL AND METHOD FOR USING THE SAME

(71) Applicant: OSSUR HF, Reykjavik (IS)

(72) Inventors: Harry Duane Romo, Aliso Viejo, CA (US); Janaki Ram-srinivasaRao Chetlapalli, Irvine, CA (US)

(73) Assignee: OSSUR HF, Reykjavik (IS)

( * ) Notice: Subject to any disclaimer, the term of this patent is extended or adjusted under 35 U.S.C. 154(b) by 311 days.

(21) Appl. No.: 14/463,726

(22) Filed: Aug. 20, 2014

(65) Prior Publication Data

US 2015/0053053 A1 Feb. 26, 2015

Related U.S. Application Data

(60) Provisional application No. 61/982,972, filed on Apr. 23, 2014, provisional application No. 61/868,659, filed on Aug. 22, 2013.

(51) Int. Cl.
*B25B 23/14* (2006.01)
*A61B 17/88* (2006.01)

(52) U.S. Cl.
CPC ...... *B25B 23/1415* (2013.01); *A61B 17/8875* (2013.01); *A61B 2090/031* (2016.02)

(58) Field of Classification Search
CPC ............. B25B 23/1415; B25B 23/142; A61B 17/8875; A61B 2090/031; A61B 17/64; A61F 5/01
See application file for complete search history.

(56) References Cited

U.S. PATENT DOCUMENTS

| | | | |
|---|---|---|---|
| 2,195,024 | A | 3/1940 | Bullock |
| 2,536,454 | A | 1/1951 | Mcintyre |
| 2,959,168 | A | 11/1960 | Shook |
| 3,331,267 | A | 7/1967 | Tietge |
| 3,444,560 | A | 5/1969 | Northup, Jr. |
| 3,753,625 | A | 8/1973 | Fabrizio et al. |
| 3,976,057 | A | 8/1976 | Barclay |
| 4,064,569 | A | 12/1977 | Campbell |
| 4,100,918 | A | 7/1978 | Glancy |
| 4,145,766 | A | 3/1979 | May |
| 4,215,600 | A | 8/1980 | Kesselman |

(Continued)

FOREIGN PATENT DOCUMENTS

| | | |
|---|---|---|
| DE | 196 31 632 A1 | 2/1998 |
| DE | 196 45 076 A1 | 5/1998 |

(Continued)

OTHER PUBLICATIONS

Defrate, Louis E., et al., "In Vivo Function of the Posterior Cruciate Ligament During Weightbearing Knee Flexion", The American Journal of Sports Medicine, Dec. 2004, pp. 1923-1928, vol. 32, No. 8, Publisher: American Orthopaedic Society for Sports Medicine, Published by SAGE; http://ajs.sagepub.com/content/32/8/1923.

(Continued)

*Primary Examiner* — David B Thomas
(74) *Attorney, Agent, or Firm* — Workman Nydegger

(57) ABSTRACT

A torque limiting tool, method for using the same, and set of torque limiting tools according to different loads are arranged for adjusting a device to a predetermined load, and preventing further adjustment once the predetermined load is reached.

17 Claims, 5 Drawing Sheets

(56) References Cited

U.S. PATENT DOCUMENTS

| | | | |
|---|---|---|---|
| 4,298,992 A | 11/1981 | Burstein et al. | |
| 4,361,142 A | 11/1982 | Lewis et al. | |
| 4,370,977 A | 2/1983 | Mauldin et al. | |
| 4,372,298 A | 2/1983 | Lerman | |
| 4,407,276 A | 10/1983 | Bledsoe | |
| 4,433,679 A | 2/1984 | Mauldin et al. | |
| 4,463,751 A | 8/1984 | Bledsoe | |
| 4,506,661 A | 3/1985 | Foster | |
| 4,520,802 A | 6/1985 | Mercer et al. | |
| 4,523,585 A | 6/1985 | Lamb et al. | |
| 4,649,906 A | 3/1987 | Spademan | |
| 4,655,201 A | 4/1987 | Pirmantgen | |
| 4,691,694 A | 9/1987 | Boyd et al. | |
| 4,697,583 A | 10/1987 | Mason et al. | |
| 4,723,539 A | 2/1988 | Townsend | |
| 4,732,143 A | 3/1988 | Kausek et al. | |
| 4,733,656 A | 3/1988 | Marquette | |
| 4,768,762 A | 9/1988 | Lund | |
| 4,773,404 A | 9/1988 | Townsend | |
| 4,790,299 A | 12/1988 | Marquette | |
| 4,793,333 A | 12/1988 | Marquette | |
| 4,817,588 A | 4/1989 | Bledsoe | |
| 4,838,264 A | 6/1989 | Bremer et al. | |
| 4,856,500 A | 8/1989 | Spadman | |
| 4,856,501 A | 8/1989 | Castillo et al. | |
| 4,865,024 A | 9/1989 | Hensley et al. | |
| 4,890,607 A | 1/1990 | Townsend | |
| 4,911,709 A | 3/1990 | Marlow et al. | |
| 4,955,369 A | 9/1990 | Bledsoe et al. | |
| 4,961,416 A | 10/1990 | Moore et al. | |
| 4,966,133 A | 10/1990 | Kausek | |
| D313,471 S | 1/1991 | Bremer et al. | |
| 4,982,732 A | 1/1991 | Morris | |
| 4,991,571 A | 2/1991 | Kausek | |
| 5,002,045 A | 3/1991 | Spademan | |
| 5,018,514 A | 5/1991 | Grood et al. | |
| 5,020,797 A | 6/1991 | Burns | |
| 5,038,765 A | 8/1991 | Young et al. | |
| 5,052,375 A | 10/1991 | Stark et al. | |
| 5,063,917 A | 11/1991 | Young et al. | |
| 5,158,458 A * | 10/1992 | Perry | A61C 8/0089 433/141 |
| 5,176,622 A | 1/1993 | Anderson et al. | |
| 5,213,094 A | 5/1993 | Bonutti | |
| 5,230,696 A | 7/1993 | Silver et al. | |
| 5,230,697 A | 7/1993 | Castillo et al. | |
| 5,261,871 A | 11/1993 | Greenfield | |
| 5,299,474 A * | 4/1994 | Hohmann | B25B 23/1415 81/467 |
| 5,347,894 A | 9/1994 | Fischer | |
| 5,357,654 A | 10/1994 | Hsing-Chi | |
| 5,437,611 A | 8/1995 | Stern | |
| 5,443,444 A | 8/1995 | Pruyssers | |
| 5,456,268 A | 10/1995 | Bonutti | |
| 5,472,410 A | 12/1995 | Hamersly | |
| 5,472,412 A | 12/1995 | Knoth | |
| 5,514,082 A | 5/1996 | Smith, III | |
| 5,588,956 A | 12/1996 | Billotti | |
| 5,599,288 A | 2/1997 | Shirley et al. | |
| 5,628,722 A | 5/1997 | Solomonow et al. | |
| 5,658,241 A | 8/1997 | Deharde et al. | |
| 5,662,596 A | 9/1997 | Young | |
| 5,685,830 A | 11/1997 | Bonutti | |
| 5,807,294 A | 9/1998 | Cawley et al. | |
| 5,827,208 A | 10/1998 | Mason et al. | |
| 5,857,988 A | 1/1999 | Shirley | |
| 5,873,847 A | 2/1999 | Bennett et al. | |
| 5,891,061 A | 4/1999 | Kaiser | |
| 5,891,071 A | 4/1999 | Sterns et al. | |
| 5,921,946 A | 7/1999 | Tillinghast et al. | |
| 5,950,245 A | 9/1999 | Binduga | |
| 5,954,677 A | 9/1999 | Albrecht et al. | |
| 5,997,493 A | 12/1999 | Young | |
| 6,004,283 A | 12/1999 | Young | |
| 6,074,355 A | 6/2000 | Bartlett | |
| 6,110,137 A | 8/2000 | Bastyr et al. | |
| 6,129,690 A | 10/2000 | Hamlin et al. | |
| RE37,209 E | 6/2001 | Hensley et al. | |
| RE37,297 E | 7/2001 | Smith, III | |
| 6,290,664 B1 | 9/2001 | Nauert | |
| 6,308,598 B1 * | 10/2001 | O'Neil | A61B 17/8875 81/439 |
| 6,331,169 B1 | 12/2001 | Bastyr et al. | |
| 6,409,693 B1 | 6/2002 | Brannigan | |
| 6,413,232 B1 | 7/2002 | Townsend et al. | |
| 6,425,166 B1 | 7/2002 | Seligman et al. | |
| 6,666,837 B2 | 12/2003 | Weihermuller | |
| 6,740,054 B2 | 5/2004 | Sterns | |
| 6,752,775 B2 | 6/2004 | Seligman et al. | |
| 6,868,757 B2 * | 3/2005 | Hufnagl | B25B 23/1415 411/38 |
| 6,875,187 B2 | 4/2005 | Castillo | |
| 6,936,020 B2 | 8/2005 | Davis | |
| 6,993,808 B1 | 2/2006 | Bennett et al. | |
| 7,004,919 B2 | 2/2006 | Gaylord et al. | |
| 7,037,287 B2 | 5/2006 | Cormier et al. | |
| 7,059,329 B2 | 6/2006 | Mason et al. | |
| 7,074,201 B2 | 7/2006 | Reinecke et al. | |
| 7,097,627 B2 | 8/2006 | Enzerink et al. | |
| 7,117,569 B2 | 10/2006 | Bledsoe | |
| 7,144,252 B2 * | 12/2006 | Walton | B25B 23/1415 433/141 |
| 7,150,721 B2 | 12/2006 | Houser | |
| 7,182,740 B1 | 2/2007 | Castillo | |
| 7,188,556 B1 * | 3/2007 | Rinner | B25B 15/02 81/467 |
| 7,192,407 B2 | 3/2007 | Seligman et al. | |
| 7,198,610 B2 | 4/2007 | Ingimundarson et al. | |
| 7,201,728 B2 | 4/2007 | Sterling | |
| 7,207,960 B2 | 4/2007 | Kenney | |
| 7,235,058 B2 | 6/2007 | Doty et al. | |
| 7,235,059 B2 | 6/2007 | Mason et al. | |
| 7,299,725 B2 * | 11/2007 | Helstern | F16B 35/06 81/468 |
| 7,308,842 B2 * | 12/2007 | Hufnagl | B25B 23/1415 411/43 |
| 7,309,322 B2 | 12/2007 | Albrecht et al. | |
| 7,311,687 B2 | 12/2007 | Hoffmeier et al. | |
| 7,431,708 B2 | 10/2008 | Sreeramagiri | |
| 7,435,234 B2 | 10/2008 | Gamada | |
| 7,485,103 B2 | 2/2009 | Mason et al. | |
| 7,500,957 B2 | 3/2009 | Bledsoe | |
| 7,534,217 B2 | 5/2009 | Seligman et al. | |
| 7,534,219 B2 | 5/2009 | Sterns | |
| 7,544,174 B2 | 6/2009 | Nathanson | |
| 7,553,289 B2 | 6/2009 | Cadichon | |
| 7,597,675 B2 | 10/2009 | Ingimundarson et al. | |
| 7,662,122 B2 | 2/2010 | Sterling | |
| 7,722,555 B2 | 5/2010 | Doty et al. | |
| 7,757,303 B2 | 7/2010 | Miller | |
| 7,806,842 B2 | 10/2010 | Stevenson et al. | |
| 7,811,242 B2 | 10/2010 | Seligman | |
| 7,846,115 B2 | 12/2010 | Seligman et al. | |
| 7,850,632 B2 | 12/2010 | Gilmour | |
| 7,927,299 B2 | 4/2011 | Krause | |
| 7,963,933 B2 | 6/2011 | Nace | |
| 8,048,013 B2 | 11/2011 | Ingimundarson et al. | |
| 8,128,587 B2 | 3/2012 | Stevenson et al. | |
| 9,044,286 B2 * | 6/2015 | O'Neil | B25B 23/1427 606/104 |
| 2002/0013544 A1 | 1/2002 | Stearns | |
| 2002/0052568 A1 | 5/2002 | Houser et al. | |
| 2002/0133108 A1 | 9/2002 | Jagodzinski | |
| 2004/0002674 A1 | 1/2004 | Sterling | |
| 2004/0049140 A1 | 3/2004 | Doty et al. | |
| 2004/0054307 A1 | 3/2004 | Mason et al. | |
| 2004/0054311 A1 | 3/2004 | Sterling | |
| 2004/0068215 A1 | 4/2004 | Adelson et al. | |
| 2004/0097859 A1 | 5/2004 | Sterns | |
| 2005/0015156 A1 | 1/2005 | Hikichi | |
| 2005/0020951 A1 | 1/2005 | Gaylord et al. | |
| 2005/0177082 A1 | 8/2005 | Bledsoe | |
| 2005/0273025 A1 | 12/2005 | Houser | |
| 2006/0100560 A1 | 5/2006 | Gilmour | |

(56) References Cited

U.S. PATENT DOCUMENTS

| | | |
|---|---|---|
| 2006/0100561 A1 | 5/2006 | Gilmour |
| 2006/0116616 A1 | 6/2006 | Albrecht et al. |
| 2006/0142680 A1 | 6/2006 | Iarocci |
| 2007/0010772 A1 | 1/2007 | Ryan |
| 2007/0100265 A1 | 5/2007 | Gamada |
| 2007/0232972 A1 | 10/2007 | Martinez |
| 2007/0270976 A1 | 11/2007 | DeHarde et al. |
| 2008/0051684 A1 | 2/2008 | Gamada |
| 2008/0249448 A1 | 10/2008 | Stevenson et al. |
| 2008/0294079 A1 | 11/2008 | Sterling et al. |
| 2009/0054819 A1 | 2/2009 | Einarsson |
| 2009/0099495 A1 | 4/2009 | Campos et al. |
| 2009/0099562 A1 | 4/2009 | Ingimundarson et al. |
| 2009/0105622 A1 | 4/2009 | Sterling et al. |
| 2009/0124948 A1 | 5/2009 | Ingimundarson et al. |
| 2009/0240181 A1 | 9/2009 | Sreeramagiri et al. |
| 2009/0259154 A1 | 10/2009 | Nace |
| 2009/0287128 A1 | 11/2009 | Ingimundarson et al. |
| 2010/0010409 A1 | 1/2010 | Bejarano |
| 2010/0056970 A1 | 3/2010 | Nace |
| 2010/0162539 A1 | 7/2010 | Rancon |
| 2011/0098618 A1 | 4/2011 | Fleming |
| 2012/0046585 A1 | 2/2012 | Lee et al. |
| 2012/0059296 A1 | 3/2012 | Kompa |
| 2013/0172797 A1 | 7/2013 | Merkley et al. |
| 2013/0178771 A1 | 7/2013 | Moir et al. |
| 2013/0331754 A1 | 12/2013 | Dunn et al. |

FOREIGN PATENT DOCUMENTS

| | | |
|---|---|---|
| DE | 198 11 925 A1 | 10/1999 |
| DE | 102 59 751 A1 | 7/2004 |
| EP | 0 841 044 A1 | 5/1998 |
| EP | 0 941 722 A1 | 9/1999 |
| EP | 1 114 619 A1 | 7/2001 |
| EP | 1 302 184 A1 | 4/2003 |
| EP | 1 575 464 A1 | 9/2005 |
| EP | 1 880 802 A2 | 1/2008 |
| EP | 2 612 624 A1 | 7/2013 |
| FR | 2 486 852 A1 | 1/1982 |
| FR | 2 663 380 A1 | 12/1991 |
| FR | 2 777 489 A1 | 10/1999 |
| FR | 2 828 093 A1 | 2/2003 |
| WO | 86/04228 A1 | 7/1986 |
| WO | 96/16615 A1 | 6/1996 |
| WO | 2004/056293 A1 | 7/2004 |
| WO | 2006/044423 A2 | 4/2006 |
| WO | 2010/087899 A2 | 8/2010 |

OTHER PUBLICATIONS

Cascade, "Jack PCL Brace", Oct. 2004, Publisher: Cascade Orthopedic Supply, Inc., Published in: US. http://www.cascade-usa.com/customer/caorsu/images/PDF/SSN_jackPCL.pdf downloaded.

Markolf, Keith L., et al., "Changes in Knee Laxity and Ligament Force After Sectioning the Posteromedial Bundle of the Posterior Cruciate Ligament", Arthroscopy: The Journal of Arthroscopic and Related Surgery, Oct. 2006, pp. 1100-1106, vol. 22, No. 10, Publisher: Arthroscopy Association of North America, Published in: US.

Papannagari, Ramprasand, et al., "Function of Posterior Cruciate Ligament Bundles During In Vivo Knee Flexion", American Journal of Sports Medicine, Sep. 2007, pp. 1507-1512, vol. 35, No. 9, Publisher: American Orthopaedic Society for Sports Medicine, Published by SAGE; http://ajs.sage.pub.com/content/35/9/1507.

Bledsoe Axiom/Axiom-D Custom 7 OTS Knee Brace, "Application Instructions & Patient Manual", Jan. 2007, pp. 1-4, vol. CP020223, Rev B, Publisher: Bledsoe Brace Systems, Published in: US. http://www.bledsoebrace.com/pdf/Al/Axiom-Al.pdf.

Brochure: Armor Fourcepoint, Donjoy Product pages http://www.donjoy.com/armorfp. Downloaded, Oct. 2011, p. 2. Published: US.

Brochure: "Fusion OA", Breg 360 Customer Care, Product page http://www.breg.com/knee-bracing/oa/fusion-oa.html, downloaded, Oct. 2011, 2 pages. Publisher: Orthofix, Published in: US.

Brochure: "Fusion XT OA", Bregg 360 Customer Care, Product page http://www.breg.com/knee-bracing/oa/fusion-xt-oa.html, downloaded, Oct. 2011, 2 pages. Publisher: Orthofix, Published in: US.

Brochure: "CTI Custom", OSSUR Product page from http://www.ossur.com/?PageID=13230 downloaded, Oct. 2011, 2 pages. Publisher: Ossur Americas, Published in: US.

Brochure: "X2K-OA", Bregg 360 Customer Care, Product page http://www.breg.com/knee-bracing/oa/x2k-oa.html. Downloaded, Oct. 2011, 1 page. Publisher: Orthofix, Published in: US.

International Search Report and Written Opinion of the International Searching Authority from International Application No. PCT/US2011/051627, Jan. 6, 2012.

International Search Report from International Application No. PCT/US2012/062702, Feb. 15, 2013.

International Preliminary Report on Patentability from International Application No. PCT/US2011/051627, Mar. 28, 2013.

Menetrey, Jacques, "PCL: Conservative Treatment", 4th Advanced Course on Knee Surgery, Jan. 22-27, 2012. http://www.kneecourse.com/download/seminar_2012/monday/MENETREY%20Conservative%20treatment.pdf.

Extended European Search Report from EP Application No. 12150517.6, May 22, 2012.

Smith, Sean D. et al., "Functional bracing of ACL injuries: current state and future directions", Knee Surgery Sports Traumatology Arthhroscopy, Springer, Apr. 27, 2013, 11 pages.

International Search Report and Written Opinion of the International Searching Authority from International Application No. PCT/US2014/013245, mailed May 6, 2014.

Jansson, Kyle S. et al., "A Historical Perspective of PCL Bracing", Knee Surgery Sports Traumatology Arthhroscopy, Springer-Verlag, May 24, 2012, 7 pages.

Knapik, Joseph J. et al., "Isometric, Isotonic and Isokinetic Torque Variations in Four Muscle Groups Through a Range of Joint Motion, Physical Therapy: Journal of the American Physical Therapy Association and de Fysiotherapeut", vol. 63, No. 6, pp. 938-947, downloaded from http://ptjournal.apta.org/ on Apr. 15, 2014.

International Search Report and Written Opinion of the International Searching Authority from Corresponding International Application No. PCT/US2014/051784, Nov. 19, 2014.

\* cited by examiner

TORQUE LIMITING TOOL AND METHOD FOR USING THE SAME

FIELD OF THE DISCLOSURE

This disclosure relates to a torque limiting tool, method for using the same, and set of torque limiting tools, and more particularly a tool arranged for adjusting a device to a predetermined load, and preventing further adjustment once the predetermined load is reached.

BACKGROUND

In certain instances, it is desired to limit the torque applied to certain devices due to possible destruction of the device or injury. In orthopedic devices, and medical devices as a whole, it is possible to exceed desirable tightening of various devices worn by a user, including pins, straps, cables, etc. If a device is over-tightened, this may cause injury to the user. Although a common tool, such as a screwdriver or wrench, may tighten devices, these common tools lack any safeguards to prevent over tightening.

While it is possible to create safeguards within the device itself, such actions have the tendency of overcomplicating the device and adding to material bulk of the device. As each individual wearer of a medical device has different anatomies and thresholds, it is difficult to provide a one-size fits all approach in design of a mechanism within the device to limit certain tightening thresholds.

Various ranges of force may be required for a device or treatment, and a single tool may not adequately permit limiting to lower or higher ranges. Current solutions do not account for different forces required for different applications and treatment stages, and are limited to a single tool that may be arranged to arbitrarily fail.

Known tools may be expensive and are general tools not specific to an application. It is desirable to provide a tool or set of tools specifically designed to handle an application while providing torque limiting means. Many tools may be expensive to make and since it is useful to provide a tool with a device, such as a knee brace, it is helpful to supply a tool or set of tools that are less expensive to make and may be disposable.

SUMMARY

According to embodiments of the disclosure, a torque limiting tool is arranged for adjusting a device to a predetermined load, and preventing further adjustment once the predetermined load is reached. The tool may shear apart once the predetermined load is reached with a handle shearing away from a key part when a predetermined magnitude of rotational force applies to the tool.

In an embodiment, the torque limiting tool includes an upper portion having a handle, a lower portion including a key part, and an intermediate portion with a shearing section and connecting the upper and lower portions.

The intermediate portion may define opposed frustoconical sections tapering toward a dividing line within the shearing section. The dividing line may be along the shearing section and adapted to shear the frustoconical sections from one another upon application of a predetermined rotational force. The frustoconical sections may have the same dimensions and may be mirror opposite one another. The frustoconical sections may have substantially continuous concentric dimensions. The torque limiting tool may be monolithic and continuously formed.

The key part may define a protruding non-cylindrical shape forming an end portion of the torque limiting tool. The key part may define a polygonal cross-section, although other shapes are likewise envisioned. The upper, intermediate and lower portions may be coaxial along a longitudinal axis of the torque limiting tool. The handle may define coaxial first and second arms along a lateral axis perpendicular to a longitudinal axis of the torque limiting tool. Each of the first and second arms may define an arcuate surface and a linear surface on opposed sides of each of the arms. The arcuate surface of the first arm may be on a side opposite to the arcuate surface of the second arm. The arcuate surface of each of the first and second arms extends along opposed sides of the longitudinal axis.

The arcuate surface of each of the first and second arms may define an arcuate segment generally concentric with the intermediate portion. The upper portion may define an upper cylindrical portion between the handle and the intermediate portion, and is generally concentric with the intermediate portion. The lower portion defines a lower cylindrical portion between the key part and the intermediate portion. The lower portion is generally concentric with the intermediate portion. The lower portion may define a lower cylindrical portion between the key part and the intermediate portion. The lower portion is generally concentric with the intermediate portion and defines a flanged surface extending generally perpendicularly to the key part.

In a method for securing a device with a torque limiting tool of any of the foregoing embodiments, the method includes coupling the key part with the rotatable receptacle, and rotating the torque limiting tool in a first rotational direction wherein at a predetermined level of rotational force, the shearing section separates the handle from the key part. The rotatable receptacle couples to a ratchet element preventing rotational movement in a second rotational direction opposite the first rotational direction. The method may further include selecting the torque limiting tool among a plurality of different torque limiting tools each having a shearing section indexed at a different predetermined level of rotational force.

A set of torque limiting tools may be provided wherein each of the torque limiting tools has a different shearing section indexed at a different predetermined level of rotational force required to shear the shearing section and sever the handle from the key part. Each of the torque limiting tools includes different indicia indicating the predetermined level of rotational force of an individual torque limiting tool.

BRIEF DESCRIPTION OF THE DRAWINGS

The torque limiting tool, the methods for using the same, and set of torque limiting tools are described referring to the accompanying drawings which show preferred embodiments. The tool, method and set as disclosed in the accompanying drawings are illustrated for example only. The elements and combinations of elements described below and illustrated in the drawings can be arranged and organized differently to result in embodiments still within the spirit and scope of the tool, method and set described.

DETAILED DESCRIPTION OF VARIOUS EMBODIMENTS

Figure 1:
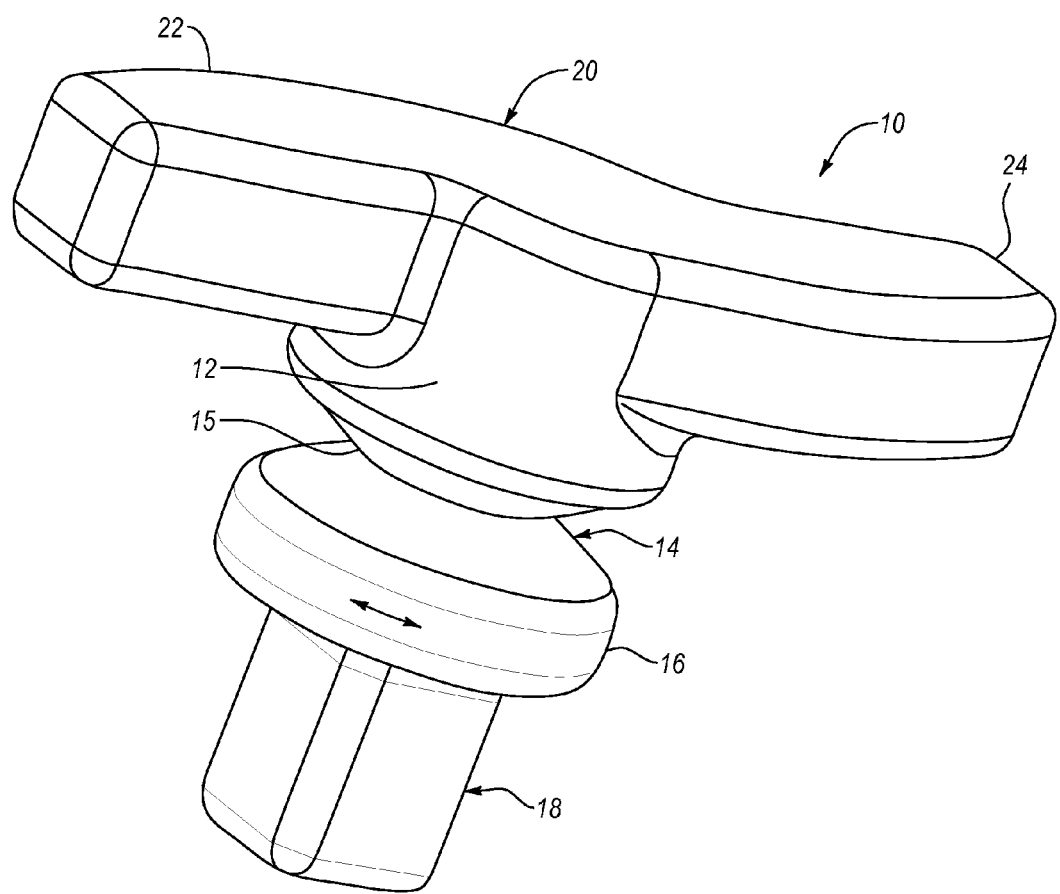
FIG. 1 is a perspective view of an embodiment of a torque limiting tool.
Figure 2:
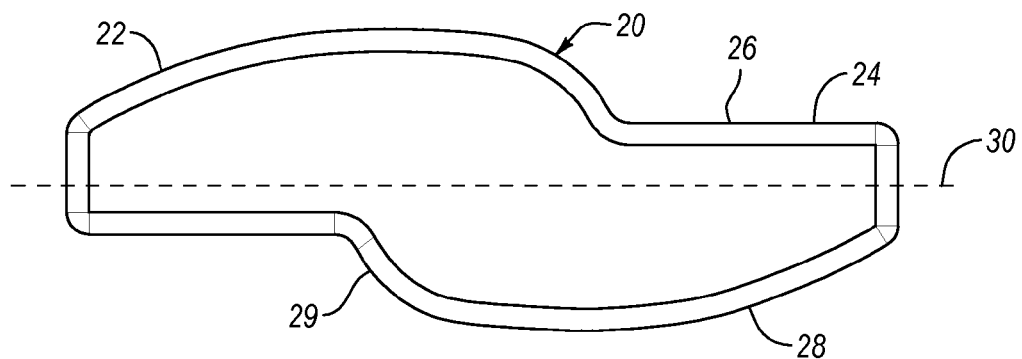
FIG. 2 is a top plan view of the torque limiting tool of FIG. 1.
Figure 3:
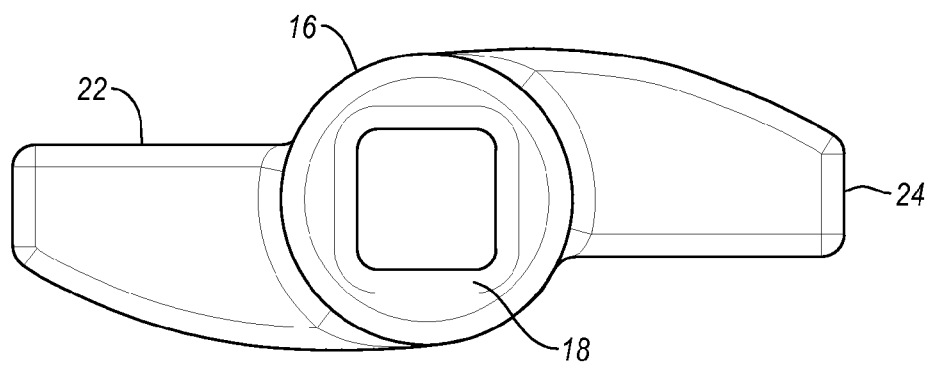
FIG. 3 is a bottom plan view of the torque limiting tool of FIG. 1.

A better understanding of different embodiments of the torque limiting tool, the methods for using the same, and set of torque limiting tools may be gained from the following description read with the accompanying drawings in which like reference characters refer to like elements.

While the disclosure is susceptible to various modifications and alternative constructions, certain illustrative embodiments are in the drawings and will be described below. It should be understood, however, there is no intention to limit the disclosure to the embodiments disclosed, but on the contrary, the invention covers all modifications, alternative constructions, combinations, and equivalents falling within the spirit and scope of the disclosure and defined by the appended claims.

It will be understood that, unless a term is defined in this disclosure to possess a described meaning, there is no intent to limit the meaning of such term, either expressly or indirectly, beyond its plain or ordinary meaning.

Referring to the embodiment of FIGS. 1-4, a torque limiting tool 10 is illustrated. The torque limiting tool 10 includes an upper portion 12 having a handle 20, a lower portion 16 including a key part 18, and an intermediate portion 14 having a shearing section 32 and connecting to the upper and lower portions 12, 16. The intermediate portion 14 defines opposed frustoconical sections 34, 36 tapering toward by a dividing line 32 defining along which lies the shearing section 15. The shearing section 15 will generally shear along or proximate to the dividing line 32.

The shearing section 15 serves as the torque limiting aspect of the tool 10 and fails upon applying a torque over a predetermined maximum amount. The shearing section 15 fails in shear so the upper portion 12 separates from the lower portion 16. When used to tighten a device, the separation of handle 20 from the key part 18 prevents a user from tightening the device beyond the predetermined amount, with the key part 18 unable to be used any further. The tool 10 may be mass produced and used with a corresponding device regardless of the circumstances of the usage of the device because the shearing section fails at the same torque.

Because the torque limiting tool is not a fastener by itself, but a tool for fastening or applying torque to a device, the key part may be configured to accommodate any mass produced receptacle. The key part can be adapted according to the receptacle, and therefore has universal application.

The frustoconical sections 34, 36 have the same dimensions and are preferably mirror opposite one another. Also, it is preferred that the frustoconical sections have substantially continuous concentric dimensions which provide uniform separation along the shearing section 15. As with the gradually reduction of material at the frustoconical sections, the separation at the shearing section is smooth to avoid abrupt breaking.

The torque limiting tool is not limited to using opposed frustoconical sections, and may merely include a shearing section having a reduced diameter between the upper and lower portions.

Figure 4:
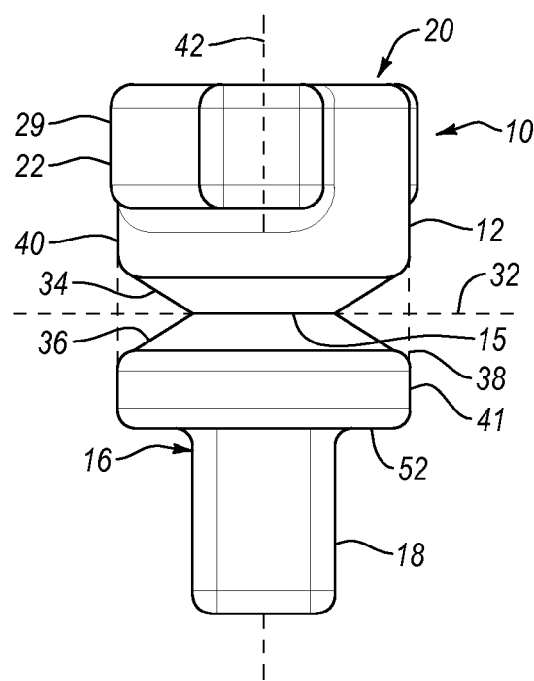
FIG. 4 is an elevational view of the torque limiting tool of FIG. 1.

As shown in FIG. 4, the upper, intermediate and lower portions are coaxial along a longitudinal axis 40 of the torque limiting tool. The upper portion 12 defines a cylindrical portion 40 between the handle 20 and the intermediate portion 14, and is concentric with the intermediate portion 14, as understood by lines 38. The handle 20 defines coaxial first and second arms 22, 24 along a lateral axis 30 perpendicular to the longitudinal axis 42.

Each of the first and second arms 22, 24 defines an arcuate surface 28 and a linear surface 26 on opposed sides of each of the arms 22, 24. The arcuate surface 28 of the first arm 22 is preferably on a side opposite to the arcuate surface 28 of the second arm 24. The arcuate surface 28 of each of the first and second arms 22, 24 extends along opposed sides of the longitudinal axis 30, and defines an arcuate segment 29 concentric with the intermediate portion 14.

The orientation of the arms of the handle provide for greater ease in tightening the key part to a receptacle, and reduces the impact of any sharp edges that may harm fingers in rotating the device. The shape of the handle is not limited to the embodiments described herein, and may be defined by a variety of shapes enabling one to grasp and turn the tool according to the manner described herein.

The lower portion 16 defines a cylindrical portion 41 between the key part 18 and the intermediate portion 14, and is concentric with the intermediate portion 14, as understood by lines 38. The cylindrical portion 41 defines a flanged surface 52 extending generally perpendicularly to the longitudinal axis 42 along which protrudes the key part 18. The flanged surface 52 is preferably substantially flat, and should extend flush with a surface of a device with which the torque limiting tool engages.

The key part 18 defines a protruding non-cylindrical shape forming an end portion of the torque limiting tool, and the shape is preferably of a polygon such as a square, hexagonal, diamond, Phillips head, etc. As shown in FIGS. 1-4, the key part defines a square cross-section. To be sufficiently robust when rotating a receptacle, the key part is preferably a solid mass with no apertures or hollow features. The key part is not limited to this construction, and may be reinforced with elements or weakened by material removal.

Figure 8:
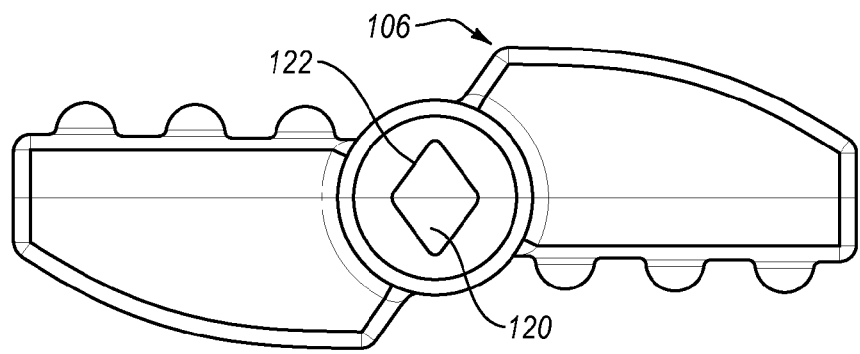
FIG. 8 is a bottom plan view showing a preferred variation of the key part.

An example of a key part 120 with a diamond profile 122 is found in FIG. 8. It is preferable that the key part 120 has a non-standard shape to prevent a user from tampering with the device. The diamond shape is generally not a standard shape and can be easily formed when molding the torque limiting tool.

The torque limiting tool is preferably monolithic and continuously formed. The torque limiting tool is formed from plastic as a solid, single body and therefore mass produced. In this manner, it is readily acceptable and cost-effective to provide a user with an abundance of torque limiting tools for each application of the device to limit effects from excessive torque. A variety of torque limiting tools may be provided each having a different threshold for separation.

As an alternative, the torque limiting tool may be reinforced with additional elements. The handle may be reinforced with a lateral bar, or the key part may be attached to the lower cylindrical portion whereby the key part is formed from a different material such as a different plastic comprising the remainder of the torque limiting tool, or a metal part.

Figure 5:
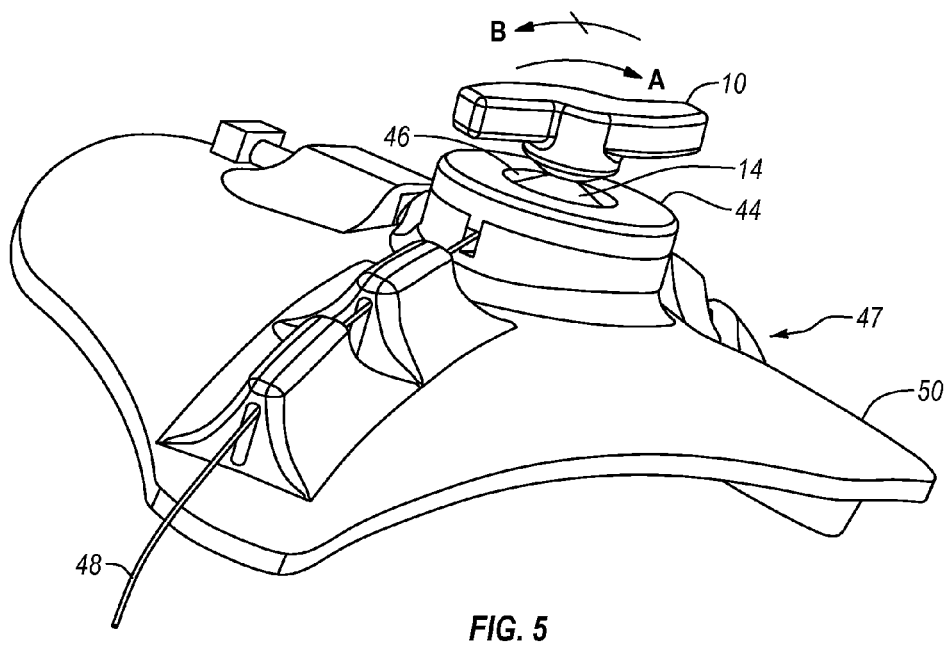
FIG. 5 is a perspective view of the torque limiting tool of FIG. 1 coupled to a receptacle of a portion of a medical device.
Figure 6:
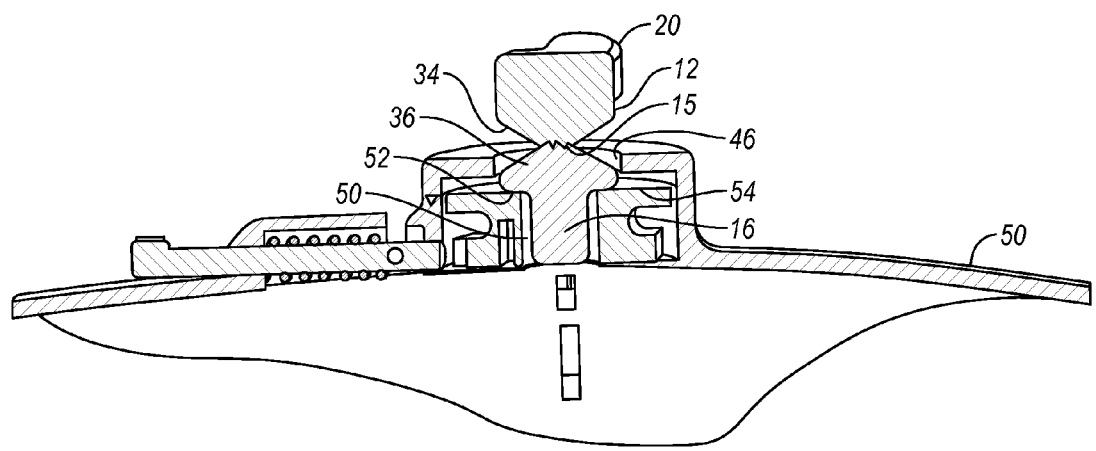
FIG. 6 is an elevational cross-sectional view of the torque limiting tool and medical device of FIG. 5.

In an example of operation, FIGS. 5 and 6 show the torque limiting tool 10 as coupled to a device part 47 of an orthopedic device described more fully in co-pending application U.S. Ser. No. 61/838,217, filed Jun. 21, 2013, and incorporated by reference.

The device part 47 is arranged as a shell that is incrementally drawn toward a tibia of a user by regulation of a cable 48 coupling to a frame of the orthopedic device (not shown). The device part 47 includes a tightening mechanism defining opening 46 through which the lower portion 16 of the torque limiting tool 10 extends to engage a receptacle 50. The receptacle 50 has a cavity dimensioned and configured to couple with the key part 18 to permit coupling in a rotational direction forming internal surfaces of the same size and shape as the key part. The tightening mechanism defines a surface 54 upon which the flanged surface 52 engages and prevents further movement of the key part into the receptacle 50.

The tightening mechanism is arranged to incrementally rotate in a first direction A and resists rotation in a second direction B unless released by release means described in Ser. No. 61/838,217. Upon excessive tightening in the first direction A, the shearing section 15 breaks and the handle and the key lock separate from one another.

The torque limiting tool is not limited to be being used in medical devices, but can be used in a variety of applications requiring limitations on torque.

Figure 7:
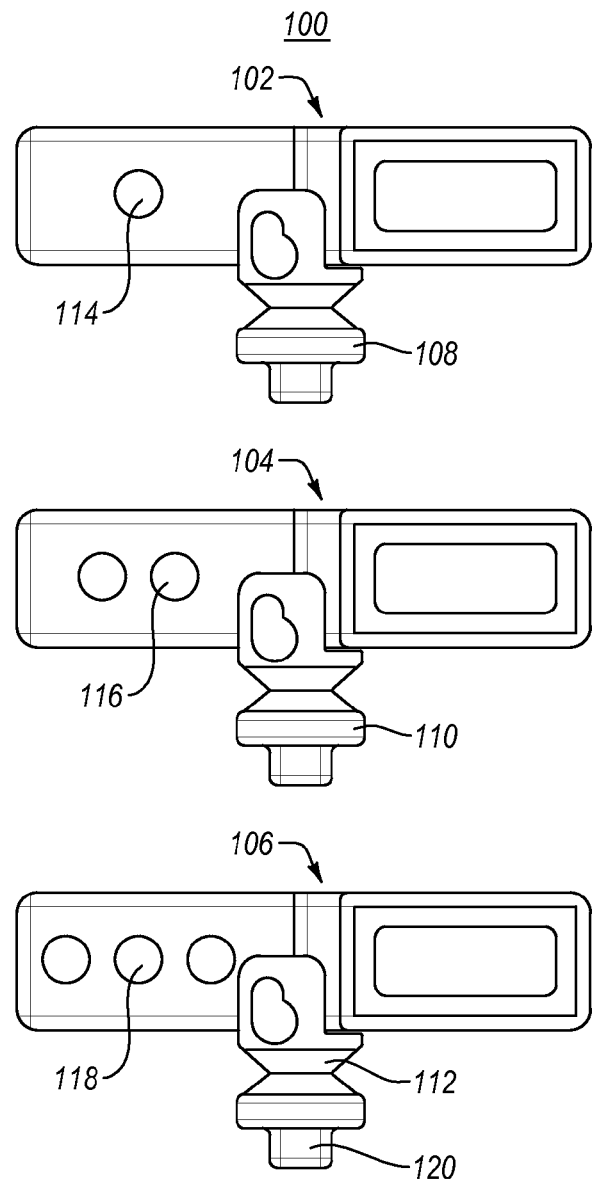
FIG. 7 is a perspective view of a set of torque limiting tools.

FIG. 7 displays a set of torque limiting tools 100 including first, second and third tools 102, 104, 106 each arranged to fail at a specified torque. The set of tools 100 may be provided with an orthopedic device to allow a user an option of different torque settings specified by a clinician. The set of torque limiting tools is not limited to three tools, and may comprise any number of tool of at least two.

Each tool has a different shearing section 108, 110, 112 defined by a different geometry. The different geometry may be defined by a shearing section with a greater diameter, thickness or other suitable means to enable a failure at a different torque.

To assist the user distinguish among the torque limiting tools, each tool may be colored differently. For example in the set 100, the first tool 102 is colored black, the second tool 104 is colored gray, and the third tool 106 is colored white. The tool set is not limited to the specified colors, and may be provided with any color scheme that distinguishes one tool from the other.

Whether provided alone or in combination with a color scheme, each tool may include indicia to denote the torque limits of each tool. The first tool 102 has indicia 114 defined by a single dot. The first tool preferably has a lower torque or load limit and the device incurs a variable load over a range of motion. Once a load is achieved, the shearing section will fail once it reaches the lower limit threshold. The second tool 104 has indicia 116 defined by two dots and preferably has a middle torque limit. The third tool 106 has indicia 118 defined by three dots and preferably has a higher torque limit. Various other indicia may denote the torque limit of each tool.

Figure 9:
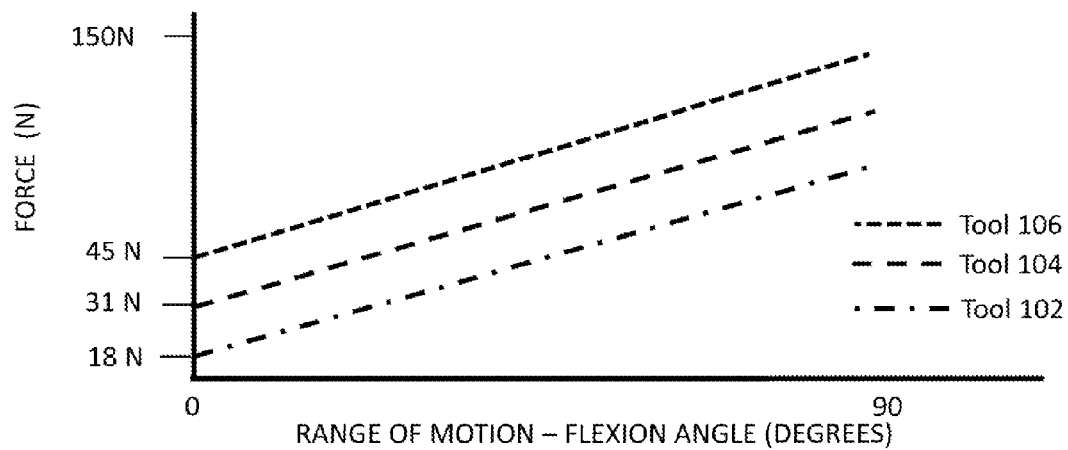
FIG. 9 is a schematic graph showing the torque loading over a range of motion for loading a functional PCL brace.

FIG. 9 shows a schematic graph showing the different loading curves for each of the tools 102, 104, 106 of the tool set 100 for loading a functional brace for a posterior cruciate ligament (PCL). The maximum torque the tool can permit the orthopedic device occurs generally at 90 degrees of flexion and once the maximum is reached, the tool will fail. In the instance of tool 106 having the highest torque limit, the force exerted on the user by the orthopedic device will be generally 150N at 90 degrees flexion, and is least at 50 N at full extension 0 degrees without generally any flexion.

Figure 10:
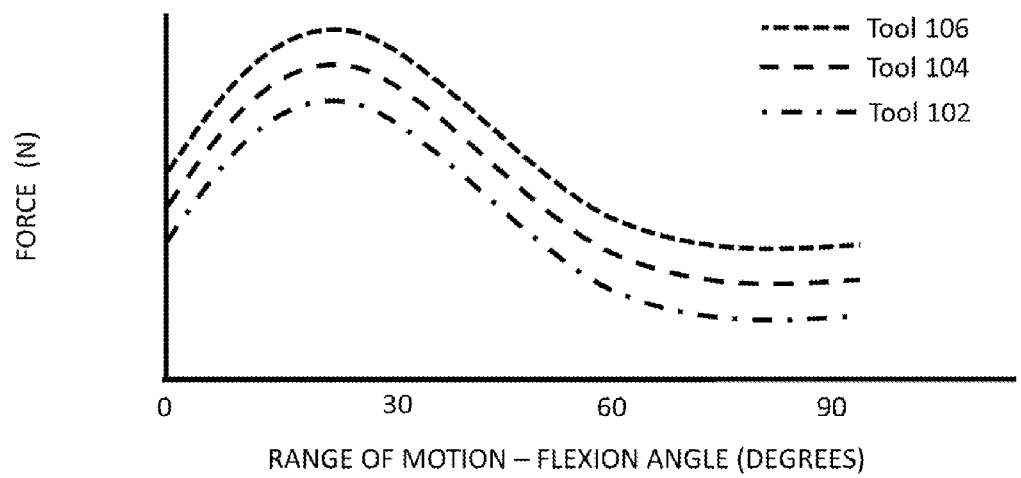
FIG. 10 is a schematic graph showing the torque loading over a range of motion for loading a functional ACL brace.

FIG. 10 is a schematic graph showing different loading curves for each of the tools 102, 104, 106 of the tool set 10 for loading a functional brace for an anterior cruciate ligament (ACL). The peak load generally occurs at 30 degrees of flexion, and generally tapers as the range of motion approaches 90 degrees. A discussion of the loading of a functional brace for an ACL is found at "Functional bracing of ACL injuries: current state and future directions," Knee Surgery, Sports Traumatology, Arthroscopy, Sean D. Smith et al., published Apr. 27, 2013.

It should be understood that not necessarily all objects or advantages may be achieved under any embodiment of the invention. Those skilled in the art will recognize that the invention may be embodied or carried out to achieve or optimizes one advantage or group of advantages as taught without achieving other objects or advantages as taught or suggested.

Those skilled in the art will recognize the interchangeability of various disclosed features. Besides the variations described, other known equivalents for each feature can be mixed and matched by one of ordinary skill under principles of the present invention.

Although this invention has been disclosed in certain exemplary embodiments and variations, it therefore will be understood by those skilled in the art that the present invention extends beyond the disclosed embodiments to other alternative embodiments and/or uses of the invention and obvious modifications and equivalents. It is intended that the present invention disclosed should not be limited by the disclosed embodiments described above.

The invention claimed is:
1. A torque limiting tool, comprising:
an upper portion having a handle;
a lower portion including a key part; and
an intermediate portion having a shearing section and connecting to the upper and lower portions;
wherein the torque limiting tool is monolithic and continuously formed.
2. The torque limiting tool of claim 1, wherein the intermediate portion defines opposed frustoconical sections tapering toward a dividing line within the shearing section.
3. The torque limiting tool of claim 2, wherein the dividing line is along the shearing section adapted to shear the frustoconical sections from one another upon application of a predetermined rotational force.
4. The torque limiting tool of claim 2, wherein the frustoconical sections have same dimensions and are mirror opposite one another.
5. The torque limiting tool of claim 2, wherein the frustoconical sections have substantially continuous concentric dimensions.
6. The torque limiting tool of claim 1, wherein the key part defines a protruding non-cylindrical shape forming an end portion of the torque limiting tool.
7. The torque limiting tool of claim 1, wherein the key part defines a polygonal cross-section.
8. The torque limiting tool of claim 1, wherein the upper, intermediate and lower portions are coaxial along a longitudinal axis of the torque limiting tool.
9. The torque limiting tool of claim 1, wherein the upper portion defines an upper cylindrical portion between the handle and the intermediate portion, and generally concentric with the intermediate portion, and the lower portion defines a lower cylindrical portion between the key part and the intermediate portion, and generally concentric with the intermediate portion.

10. The torque limiting tool of claim 1, wherein the lower portion defines a lower cylindrical portion between the key part and the intermediate portion, and generally concentric with the intermediate portion, the lower cylindrical portion defines a flanged surface extending generally perpendicularly to the key part.

11. A torque limiting tool, comprising:
an upper portion having a handle;
a lower portion including a key part; and
an intermediate portion having a shearing section and connecting to the upper and lower portions;
wherein each of the first and second arms defines an arcuate surface and a linear surface on opposed sides of each of the arms, the arcuate surface of the first arm is on a side opposite to the arcuate surface of the second arm;
wherein the handle defines coaxial first and second arms along a lateral axis perpendicular to a longitudinal axis of the torque limiting tool.

12. The torque limiting tool of claim 11, wherein the arcuate surface of each of the first and second arms extends along opposed sides of the longitudinal axis.

13. The torque limiting tool of claim 11, wherein the arcuate surface of each of the first and second arms defines an arcuate segment generally concentric with the intermediate portion.

14. A method for securing a device with a torque limiting tool having a handle, a key part and a shearing section, the device including a rotatable receptacle for correspondingly receiving the key part, the method comprising the steps of:

coupling the key part with the rotatable receptacle;
rotating the torque limiting tool in a first rotational direction wherein at a predetermined level of rotational force, the shearing section separates the handle from the key part;
wherein the rotatable receptacle couples to a ratchet element preventing rotational movement in a second rotational direction opposite the first rotational direction.

15. The method of claim 14, further comprising the step of:
selecting the torque limiting tool among a plurality of different torque limiting tools each having a shearing section indexed at a different predetermined level of rotational force.

16. A set of torque limiting tools, each of the torque limiting tools including an upper portion having a handle, a lower portion including a key part, and
an intermediate portion having a shearing section and connecting to the upper and lower portions;
wherein each of the torque limiting tools is monolithic and continuously formed;
wherein each of the torque limiting tools has a different shearing section indexed at a different predetermined level of rotational force required to shear the shearing section and sever the handle from the key part.

17. The set of torque limiting tools of claim 16, wherein each of the torque limiting tools includes different indicia indicating the predetermined level of rotational force of an individual torque limiting tool.

* * * * *